United States Patent
Hasegawa

(10) Patent No.: US 11,864,843 B2
(45) Date of Patent: Jan. 9, 2024

(54) IMAGE DIAGNOSIS SUPPORT APPARATUS, IMAGE DIAGNOSIS SUPPORT METHOD, IMAGE DIAGNOSIS SUPPORT PROGRAM, AND HEART SIMULATION SYSTEM

(71) Applicant: FUJIFILM Corporation, Tokyo (JP)

(72) Inventor: Yu Hasegawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 439 days.

(21) Appl. No.: 17/143,166

(22) Filed: Jan. 7, 2021

(65) Prior Publication Data
US 2021/0121241 A1    Apr. 29, 2021

Related U.S. Application Data

(63) Continuation of application No. PCT/JP2019/027200, filed on Jul. 9, 2019.

(30) Foreign Application Priority Data

Jul. 13, 2018    (JP) .................................. 2018-132893

(51) Int. Cl.
*A61B 5/00*    (2006.01)
*A61B 34/20*   (2016.01)
(Continued)

(52) U.S. Cl.
CPC .............. *A61B 34/20* (2016.02); *A61N 1/056* (2013.01); *G06T 7/62* (2017.01); *G06T 2200/04* (2013.01);
(Continued)

(58) Field of Classification Search
CPC ....... A61B 34/20; G06T 7/62; G06T 2200/04; G06T 2207/30048; G06T 2207/30101; A61N 1/056
See application file for complete search history.

(56) References Cited

U.S. PATENT DOCUMENTS 6,885,889 B2    4/2005 Chinchoy
2015/0119966 A1*  4/2015 Richter .................. A61B 34/10
                                                  607/122
(Continued)

FOREIGN PATENT DOCUMENTS

EP    2486952       8/2012
JP    2005338551    12/2005
(Continued)

OTHER PUBLICATIONS

"International Search Report (Form PCT/ISA/210) of PCT/JP2019/027200," dated Oct. 8, 2019, with English translation thereof, pp. 1-6.
(Continued)

*Primary Examiner* — Joel F Brutus
(74) *Attorney, Agent, or Firm* — JCIPRNET

(57) ABSTRACT

An image diagnosis support apparatus includes a shape information acquiring unit that acquires shape information including a size of a diameter and a route of a coronary vein for at least one coronary vein from a three-dimensional image including a heart, a distal position acquiring unit that acquires a most distal position into which an electrode lead wire having a plurality of electrodes arranged at predetermined electrode intervals is able to be inserted based on the shape information, and information indicating a size of a diameter of the electrode lead wire, and a candidate position acquiring unit that acquires at least one piece of information indicating candidate positions of the plurality of electrodes which are candidates for positioning the plurality of electrodes in the coronary vein based on the distal position and positional information indicating arrangement positions of the plurality of electrodes.

20 Claims, 11 Drawing Sheets

(51) Int. Cl.
*G06T 7/62* (2017.01)
*A61N 1/05* (2006.01)

(52) U.S. Cl.
CPC ........... *G06T 2207/30048* (2013.01); *G06T 2207/30101* (2013.01)

(56) References Cited

U.S. PATENT DOCUMENTS

| | | | |
|---|---|---|---|
| 2017/0032095 A1* | 2/2017 | Kadooka | G06Q 10/10 |
| 2017/0065242 A1 | 3/2017 | Chirvasa et al. | |
| 2017/0347980 A1 | 12/2017 | Wakai | |

FOREIGN PATENT DOCUMENTS

| | | |
|---|---|---|
| JP | 2006519085 | 8/2006 |
| JP | 2012166029 | 9/2012 |
| JP | 2017033227 | 2/2017 |
| JP | 2017217474 | 12/2017 |

OTHER PUBLICATIONS

"Written Opinion of the International Searching Authority (Form PCT/ISA/237) of PCT/JP2019/027200," dated Oct. 8, 2019, with English translation thereof, pp. 1-9.

Nirmal Panthee et al., "Tailor-made heart simulation predicts the effect of cardiac resynchronization therapy in a canine model of heart failure", Medical Image Analysis, Feb. 2016, pp. 46-62.

Wouter M. Van Everdingen et al., "Quadripolar Leads in Cardiac Resynchronization Therapy", JACC: Clinical Electrophysiology, Aug. 2015, pp. 225-237.

Michael Seger et al., "Non-invasive imaging of cardiac electrophysiology in a cardiac resynchronization therapy defibrillator patient with a quadripolar left ventricular lead", Europace, May 2014, pp. 743-749.

Office Action of Japan Counterpart Application, with English translation thereof, dated Feb. 8, 2022, pp. 1-13.

Office Action of Japan Counterpart Application, with English translation thereof, dated Nov. 9, 2021, pp. 1-9.

* cited by examiner

IMAGE DIAGNOSIS SUPPORT APPARATUS, IMAGE DIAGNOSIS SUPPORT METHOD, IMAGE DIAGNOSIS SUPPORT PROGRAM, AND HEART SIMULATION SYSTEM

CROSS-REFERENCE TO RELATED APPLICATIONS

This application is a Continuation of PCT International Application No. PCT/JP2019/027200 filed on Jul. 9, 2019, which claims priority under 35 U.S.C. § 119(a) to Japanese Patent Application No. 2018-132893 filed on Jul. 13, 2018. Each of the above application(s) is hereby expressly incorporated by reference, in its entirety, into the present application.

BACKGROUND OF THE INVENTION

1. Field of the Invention

The present disclosure relates to an image diagnosis support apparatus, an image diagnosis support method, a non-transitory computer recording medium storing an image diagnosis support program, and a heart simulation system.

2. Description of the Related Art

In the recent years, a treatment method called cardiac resynchronization therapy (CRT) of performing, for patient who have some kind of failure in the pump function of the heart, correcting of the deviation of the contraction timing in the heart with a pacemaker to recover the pump function close to normal has been performed. However, there is a report that the CRT is not an effective treatment method for all patients, and even in a case where the latest device is used, improvement of cardiac function is not observed in about 30% of patients. Further, in the CRT, since it is necessary to place the electrode lead wires in the right ventricle, the right atrium, and the left ventricle respectively, considering the risk of complications in a case of placing the electrode lead wires, it is desired to improve the accuracy of prediction for predicting the effect of the CRT in advance in order to determine the necessity of the CRT. As a method for predicting the effects of the CRT, currently, a method is studied and developed in which the reactivity of the heart in a case where the CRT is actually performed is determined using a simulator that reproduces a heart peculiar to a patient electrophysiologically and mechanically.

In the CRT, the electrode lead wire placed in the left ventricle is generally placed in the coronary vein. The reactivity of the heart in the CRT depends on the position of placing the electrode of the electrode lead wire placed in the left ventricle. Therefore, in recent years, as the electrode lead wire placed in the left ventricle, as shown in FIG. 12, there is an electrode lead wire 7 in which four electrodes A1 to A4 are arranged with an interval a therebetween of 12 mm in a case where a length L is 40 mm. In the electrode lead wire 7, after being placed in the left ventricle, the electrode to be used can be selected from four electrodes A1 to A4, and thereby the reactivity of the heart is enhanced.

Also in the CRT simulation using the simulator, bringing the positions of a plurality of electrodes of the electrode lead wire placed in the left ventricle close to the position to be placed in a case where the CRT is actually performed improves the accuracy of the simulation, and is important to reduce the proportion of patients who have no improvement in cardiac function.

On the other hand, there has been known an intervention surgery in which a medical image diagnosis apparatus such as an X-ray fluoroscopic apparatus captures an image of the inside of a subject in real time, and inserts a treatment device into the subject while referring to images sequentially displayed in time series. JP2017-217474A discloses a medical image diagnosis apparatus that detects a position of the treatment device in the medical image, and displays the position of the treatment device and a biomarker associated with the position of the treatment device during intervention surgery. In the medical image diagnosis apparatus disclosed in JP2017-217474A, an anatomical characteristic site such as a coronary vein is specified from a real-time image and a pre-acquired image, and a placement candidate position of the tip of the electrode lead wire is obtained.

SUMMARY OF THE INVENTION

However, in the medical image diagnosis apparatus JP2017-217474A, the placement candidate position of the tip of the electrode lead wire is required during the intervention surgery. That is, since the placement candidate position is obtained in a state where the electrode lead wire is inserted into the subject, the electrode lead wire may be inserted into the body even for a patient whose cardiac function is not improved even after performing the CRT, and thus a risk of complications may occur.

The present disclosure has been made in view of the above circumstances, and is to enable decision of a candidate position for placing an electrode before the CRT is performed.

An image diagnosis support apparatus according to an aspect of the present disclosure comprises a shape information acquiring unit that acquires shape information including a size of a diameter and a route of a coronary vein for at least one coronary vein from a three-dimensional image including a heart, a distal position acquiring unit that acquires a most distal position into which an electrode lead wire having a plurality of electrodes arranged at predetermined electrode intervals is able to be inserted in an insertion direction of the electrode lead wire based on the shape information acquired by the shape information acquiring unit, and information indicating a size of a diameter of the electrode lead wire, and a candidate position acquiring unit that acquires at least one piece of information indicating candidate positions of the plurality of electrodes which are candidates for positioning the plurality of electrodes in the coronary vein based on the distal position and positional information indicating arrangement positions of the plurality of electrodes.

The image diagnosis support apparatus according to the aspect of the present disclosure, the candidate position acquiring unit may acquire, for each coronary vein, the information indicating the candidate positions of the plurality of electrodes at positions traced back to a proximal side from the distal position on the route of the coronary vein.

The image diagnosis support apparatus according to the aspect of the present disclosure, the candidate position acquiring unit may acquire, for each coronary vein, the information indicating the candidate position of the electrode located on a most distal side among the plurality of electrodes within a predetermined range including the distal position.

In the image diagnosis support apparatus according to the aspect of the present disclosure, the candidate position acquiring unit may acquire the candidate position of the electrode in a candidate range which is predetermined (predetermined candidate range), and acquire information indicating the candidate position acquired in the candidate range as the information indicating the candidate position of the electrode.

In the image diagnosis support apparatus according to the aspect of the present disclosure, the candidate position acquiring unit may acquire the information indicating the candidate positions of the plurality of electrodes at positions distant from the distal position by a predetermined distance to the proximal side.

In the image diagnosis support apparatus according to the aspect of the present disclosure, the distal position acquiring unit may enable insertion of the electrode lead wire in the coronary vein in a case where the diameter of the coronary vein is larger than the diameter of the electrode lead wire.

In the image diagnosis support apparatus according to the aspect of the present disclosure, the electrode lead wire may have flexibility, and the distal position acquiring unit may enable insertion of the electrode lead wire in the coronary vein in a case where the electrode lead wire has the flexibility adaptable to a curvature of the coronary vein.

In the image diagnosis support apparatus according to the aspect of the present disclosure, the candidate position acquiring unit may exclude the candidate position of the electrode from a candidate for electrode arrangement in a case where the candidate position of the electrode is located within a myocardial infarction area in the three-dimensional image.

The image diagnosis support apparatus according to the aspect of the present disclosure may further comprise a display control unit that performs control of displaying the three-dimensional image and the candidate position of the electrode on a display unit.

In the image diagnosis support apparatus according to the aspect of the present disclosure, the display control unit may perform control of displaying the candidate position of the electrode while superimposing the candidate position of the electrode on the three-dimensional image.

The image diagnosis support apparatus according to the aspect of the present disclosure may further comprise an output unit that outputs at least one piece of positional information of the candidate positions of the electrodes acquired by the candidate position acquiring unit.

A heart simulation system according to another aspect of the present disclosure comprises the image diagnosis support apparatus according to the above aspect, and a simulator that includes a receiving unit receiving at least one piece of positional information of the candidate positions of the electrodes output from the image diagnosis support apparatus, and disposes the electrode at each candidate position of the electrode based on the at least one piece of positional information of the candidate positions of the electrodes received by the receiving unit, and reproduces a cardiac motion peculiar to a patient who is a target of the three-dimensional image.

An image diagnosis support method according to still another aspect of the present disclosure comprises acquiring shape information including a size of a diameter and a route of a coronary vein for at least one coronary vein from a three-dimensional image including a heart, acquiring a most distal position into which an electrode lead wire having a plurality of electrodes arranged at predetermined electrode intervals is able to be inserted in an insertion direction of the electrode lead wire based on the acquired shape information, and information indicating a size of a diameter of the electrode lead wire, and acquiring at least one piece of information indicating candidate positions of the plurality of electrodes which are candidates for positioning the plurality of electrodes in the coronary vein based on the distal position and positional information indicating arrangement positions of the plurality of electrodes.

A non-transitory computer recording medium storing an image diagnosis support program according to still another aspect of the present disclosure causes a computer to execute a procedure of acquiring shape information including a size of a diameter and a route of a coronary vein for at least one coronary vein from a three-dimensional image including a heart, a procedure of acquiring a most distal position into which an electrode lead wire having a plurality of electrodes arranged at predetermined electrode intervals is able to be inserted in an insertion direction of the electrode lead wire based on the acquired shape information, and information indicating a size of a diameter of the electrode lead wire, and a procedure of acquiring at least one piece of information indicating candidate positions of the plurality of electrodes which are candidates for positioning the plurality of electrodes in the coronary vein based on the distal position and positional information indicating arrangement positions of the plurality of electrodes.

Another image diagnosis support apparatus according to still another aspect of the present disclosure comprises a memory that stores a command to be executed by a computer, and a processor that executes the stored command, in which the processor executes processing of acquiring shape information including a size of a diameter and a route of a coronary vein for at least one coronary vein from a three-dimensional image including a heart, acquiring a most distal position into which an electrode lead wire having a plurality of electrodes arranged at predetermined electrode intervals is able to be inserted based on the acquired shape information, and information indicating a size of a diameter of the electrode lead wire, and acquiring at least one piece of information indicating candidate positions of the plurality of electrodes which are candidates for positioning the plurality of electrodes in the coronary vein based on the distal position and positional information indicating arrangement positions of the plurality of electrodes.

In the aspect of the present disclosure, processing is performed in which shape information including a size of a diameter and a route of a coronary vein is acquired for at least one coronary vein from a three-dimensional image including a heart, a most distal position into which an electrode lead wire having a plurality of electrodes arranged at predetermined electrode intervals is able to be inserted is acquired based on the acquired shape information, and information indicating a size of a diameter of the electrode lead wire, and at least one piece of information indicating candidate positions of the plurality of electrodes which are candidates for positioning the plurality of electrodes in the coronary vein is acquired based on the distal position and positional information indicating arrangement positions of the plurality of electrodes. Thus, it is possible to decide a candidate position in which an electrode is placed in a case of actually performing the CRT, before the CRT is performed. Therefore, the simulator can perform the simulation at a position in which the electrode is placed before the CRT is actually performed, and thus the accuracy of the simulation can be improved.

DESCRIPTION OF THE PREFERRED EMBODIMENTS

Figure 1:
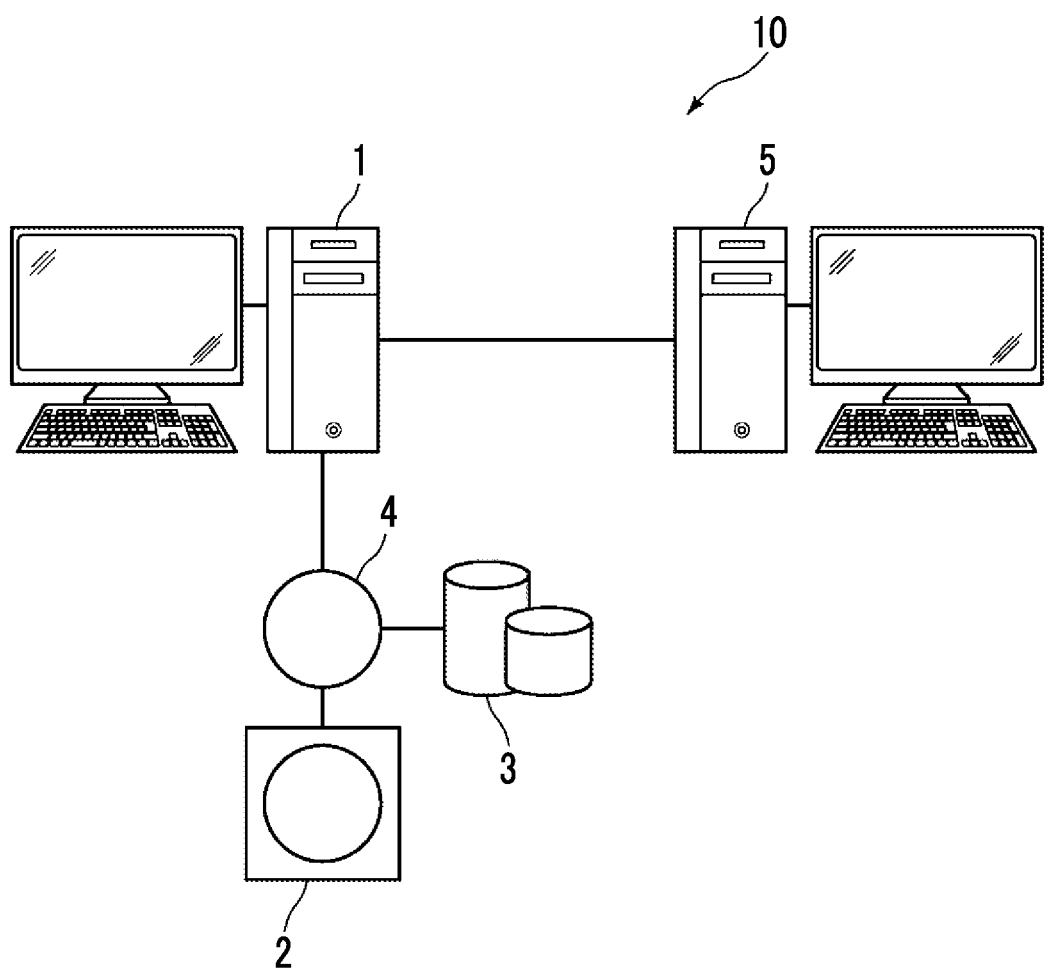
FIG. 1 is a hardware configuration diagram showing an outline of a heart simulation system to which an image diagnosis support apparatus according to an embodiment of the present disclosure is applied.

Hereinafter, a first embodiment of the present disclosure will be described with reference to the drawings. FIG. 1 is a hardware configuration diagram showing an outline of a heart simulation system to which an image diagnosis support apparatus according to an embodiment of the present disclosure is applied. As shown in FIG. 1, in a heart simulation system 10, an image diagnosis support apparatus 1 according to a first embodiment, a three-dimensional image capturing apparatus 2, and an image storage server 3 are connected in a communicable state via a network 4. The heart simulation system 10 comprises a simulator 5 connected to the image diagnosis support apparatus 1 by wireless or wire. In the heart simulation system 10, the simulator 5 performs simulation of placing electrodes at positions close to the positions of a plurality of electrodes of an electrode lead wire placed in the left ventricle of the heart of a subject in a case of actually performing the CRT using a three-dimensional image of the subject's heart.

The three-dimensional image capturing apparatus 2 is an apparatus that images a diagnosis target site of a subject to generate the three-dimensional image showing the site, and a specific example thereof includes a CT apparatus, a magnetic resonance imaging (MRI) apparatus, and a positron emission tomography (PET) apparatus.

The three-dimensional image generated by the three-dimensional image capturing apparatus 2 is transmitted to the image storage server 3 and stored therein. In the first embodiment, the place where the electrode of the electrode lead wire is installed is a coronary vein of the subject's heart, and thus the diagnosis target site of the subject is chest including the coronary vein.

The three-dimensional image capturing apparatus 2 is the CT apparatus, and generates the three-dimensional image including a plurality of tomographic images of axial cross sections of the chest of the subject.

The image storage server 3 is a computer that stores and manages various data, and comprises a large capacity external storage device and database management software. The image storage server 3 communicates with other devices via the wired or wireless network 4 to transmit and receive image data. Specifically, the image storage server 3 acquires the image data such as the three-dimensional image generated by the three-dimensional image capturing apparatus 2 via the network, and stores and manages the image data in a recording medium such as the large capacity external storage device. The storage format of the image data and communication between the devices via the network 4 are based on a protocol such as digital imaging and communication in medicine (DICOM).

The image diagnosis support apparatus 1 is an apparatus in which an image diagnosis support program according to the present disclosure is installed in one computer. The computer may be a workstation or a personal computer directly operated by a doctor who makes a diagnosis, or a server computer connected to the workstation or the personal computer via the network. The image diagnosis support program is recorded in a recording medium such as a digital versatile disc (DVD) or a compact disc read only memory (CD-ROM) to be distributed, and is installed in the computer from the recording medium. Alternatively, the program is stored in the storage device of the server computer connected to the network or the network storage so as to be accessible from the outside, and is downloaded and installed in the computer used by a doctor upon request.

Figure 2:
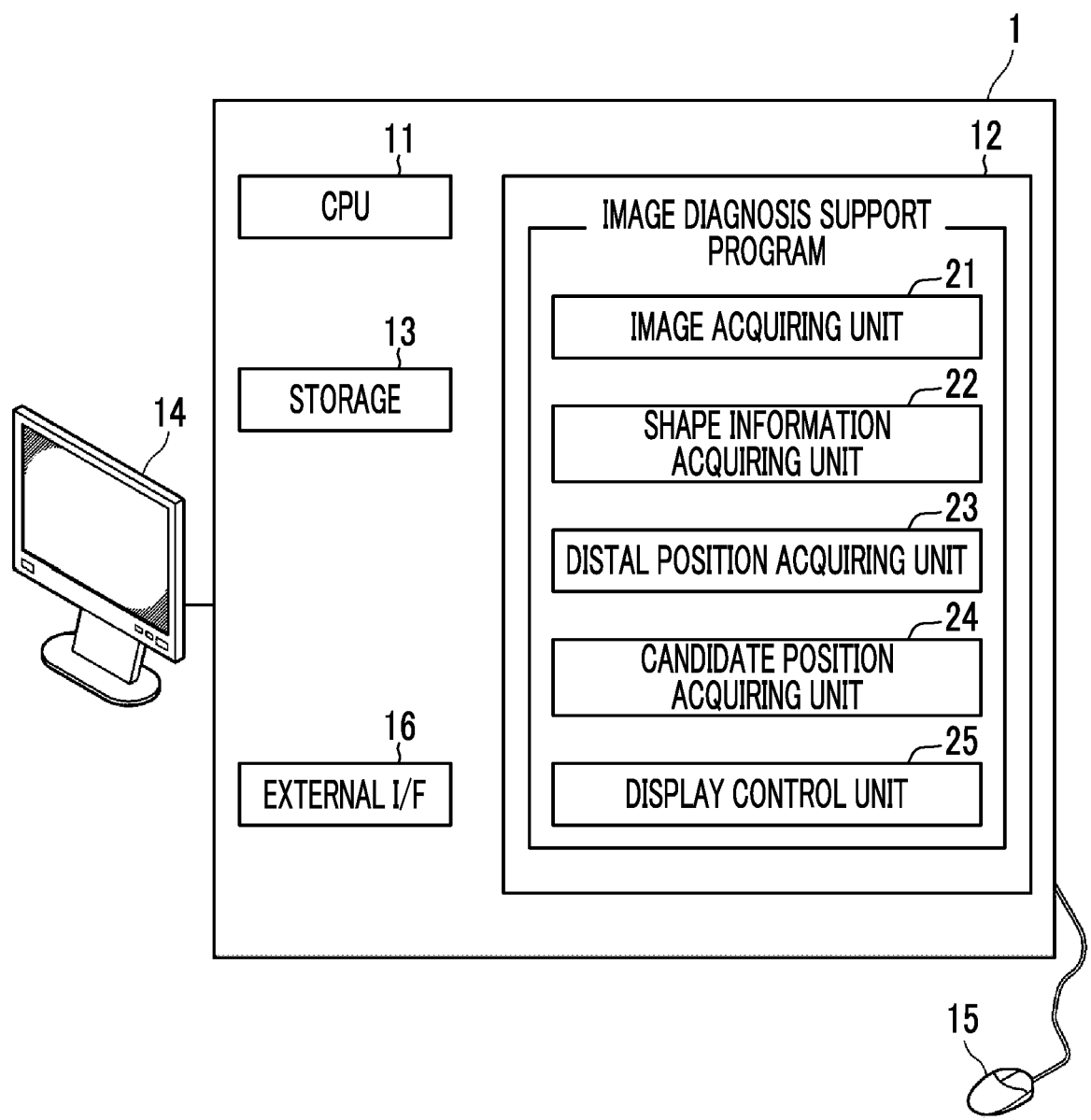
FIG. 2 is a diagram showing a schematic configuration of the image diagnosis support apparatus according to the embodiment of the present disclosure.

FIG. 2 is a diagram showing a schematic configuration of the image diagnosis support apparatus according to the first embodiment, which is realized by installing the image diagnosis support program in the computer. As shown in FIG. 2, the image diagnosis support apparatus 1 comprises a central processing unit (CPU) 11, a memory 12, a storage 13, and an external interface (I/F) 16, as a standard configuration of the workstation. Also, the image diagnosis support apparatus 1 is connected with a display (display unit) 14 such as a liquid crystal display, and an input unit 15 such as a keyboard or a mouse.

Figure 12:
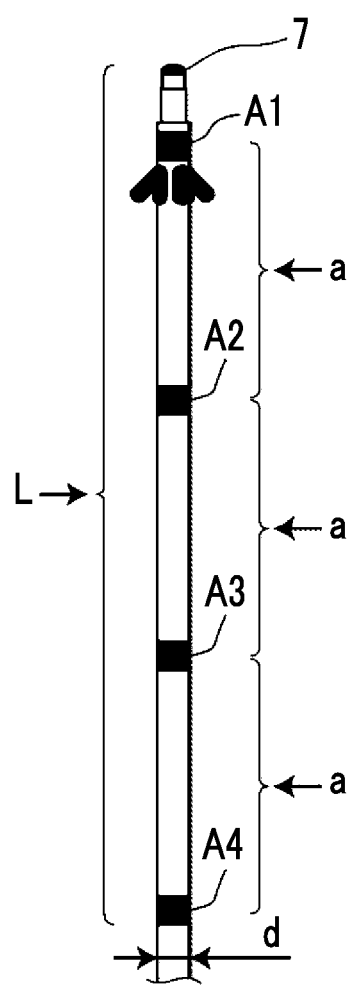
FIG. 12 is a diagram showing an example of an electrode lead wire.

The storage 13 includes the storage device such as a hard disk, and a solid state drive (SSD). The storage 13 stores various information including the three-dimensional image of the subject and information necessary for processing, which are acquired from the image storage server 3 via the network 4. In the first embodiment, a diameter d and a length L of an electrode lead wire 7, and positional information of four electrodes A1 to A4 including an interval a therebetween shown in FIG. 12 are stored. The electrode lead wire 7 has flexibility, an index indicating the flexibility of the electrode lead wire 7 is stored in the storage 13. Here, the index indicating the flexibility can be the maximum value of the curvature of the electrode lead wire 7, for example.

The external I/F 16 controls transmission and reception of various information between the image diagnosis support apparatus 1 and the simulator 5. The external I/F 16 functions as an output unit according to the present disclosure, which outputs at least one piece of positional information of candidate positions of the electrodes acquired by a candidate position acquiring unit 24 described below.

The image diagnosis support program is stored in the memory 12. An image diagnosis support program defines, as processing executed by the CPU 11, an image acquisition processing of acquiring the three-dimensional image including the heart, shape information acquisition processing of acquiring shape information including a size of a diameter and a route of a coronary vein for at least one coronary vein from the three-dimensional image including the heart, distal position acquisition processing of acquiring a most distal position into which an electrode lead wire having a plurality of electrodes arranged at predetermined electrode intervals can be inserted based on the acquired shape information, and information indicating a size of a diameter of the electrode lead wire, candidate position acquisition processing of acquiring at least one piece of information indicating candidate positions of the plurality of electrodes which are candidates for positioning the plurality of electrodes in the coronary vein based on the distal position and positional information indicating arrangement positions of the plurality of electrodes, and display control processing of performing control of displaying the three-dimensional image and the candidate positions of the electrodes on the display 14.

The CPU 11 executes processing in response to the program, and the computer functions as an image acquiring unit 21, a shape information acquiring unit 22, a distal position acquiring unit 23, the candidate position acquiring unit 24, and a display control unit 25. In the first embodiment, the functions of units is executed by the image diagnosis support program, but the present disclosure is not limited thereto, for example, the functions of the units may be executed by appropriate combinations of a plurality of integrated circuits (IC), a processor, an application specific integrated circuit (ASIC), a field-programmable gate array (FPGA), and the memory.

The image acquiring unit 21 acquires the three-dimensional image of the subject's chest from the image storage server 3 in order to place the electrodes of the electrode lead wire. In a case where the three-dimensional image is stored in the storage 13 in advance, the image acquiring unit 21 may acquire the three-dimensional image from the storage 13. In the first embodiment, the three-dimensional image acquired by the image acquiring unit 21 is a CT image, and the image acquiring unit 21 acquires the CT image acquired by the three-dimensional image capturing apparatus 2 in a state where the contrast agent is administered to the subject. Generally, the timing of imaging a coronary artery and the timing of imaging a coronary vein are different, and thus the image acquiring unit 21 acquires the CT image acquired by the three-dimensional image capturing apparatus 2 at the timing of imaging the coronary vein.

The shape information acquiring unit 22 acquires shape information including a size of a diameter and a route of a coronary vein for at least one coronary vein from the CT image including the heart. Specifically, a coronary vein area is extracted as a blood vessel area from the CT image acquired by the image acquiring unit 21 using known technology. For example, even in a case where the blood vessel radius is the same in the imaged CT image for coronary vein analysis, the brightness values of the artery is lower than that of the vein. By utilizing this feature, the coronary artery and the coronary vein can be separated and extracted in the CT image. By using the method disclosed in JP2011-098195A, for example, the coronary vein and the coronary artery can be discriminated and detected in the CT image. The method of extracting coronary artery area in the three-dimensional image is generally known as disclosed in JP2012-085721A, and in a case where the coronary vein area and the coronary artery area are mixed in the CT image, the coronary vein area may be extracted by extracting and removing the coronary artery area from the CT image.

The shape information acquiring unit 22 extracts a central line in the extracted coronary vein area by the known method to acquire the positional information of the central line as route information. The shape information acquiring unit 22 acquires the size of the diameter in the extracted coronary vein area at regular intervals. The area of the cross section perpendicular to the central line or the perimeter of the cross section is measured, and the size of the diameter can be calculated from the measured area or perimeter, but the method is not limited thereto, and a known method may be used. The interval at which the size of the diameter is acquired can be optionally changed by the operator.

The distal position acquiring unit 23 acquires the most distal position into which the electrode lead wire 7 can be inserted based on the shape information acquired by the shape information acquiring unit 22, and the information indicating the size of the diameter d of the electrode lead wire 7 stored in the storage 13. The method of acquiring the distal position by the distal position acquiring unit 23 will be described in detail below.

The candidate position acquiring unit 24 acquires at least one piece of the information indicating the candidate positions of a plurality of electrodes A1 to A4, which are candidates for positioning a plurality of electrodes A1 to A4 in the coronary vein based on the distal position and the positional information indicating the arrangement position of a plurality of electrodes A1 to A4 of the electrode lead wire 7 stored in the storage 13. The method of acquiring the candidate position by the candidate position acquiring unit 24 will be described in detail below.

The display control unit 25 performs control of displaying the CT image and the candidate positions of the electrodes on the display 14. The display control unit 25 performs control of displaying various information necessary for processing in the display 14.

Figure 3:
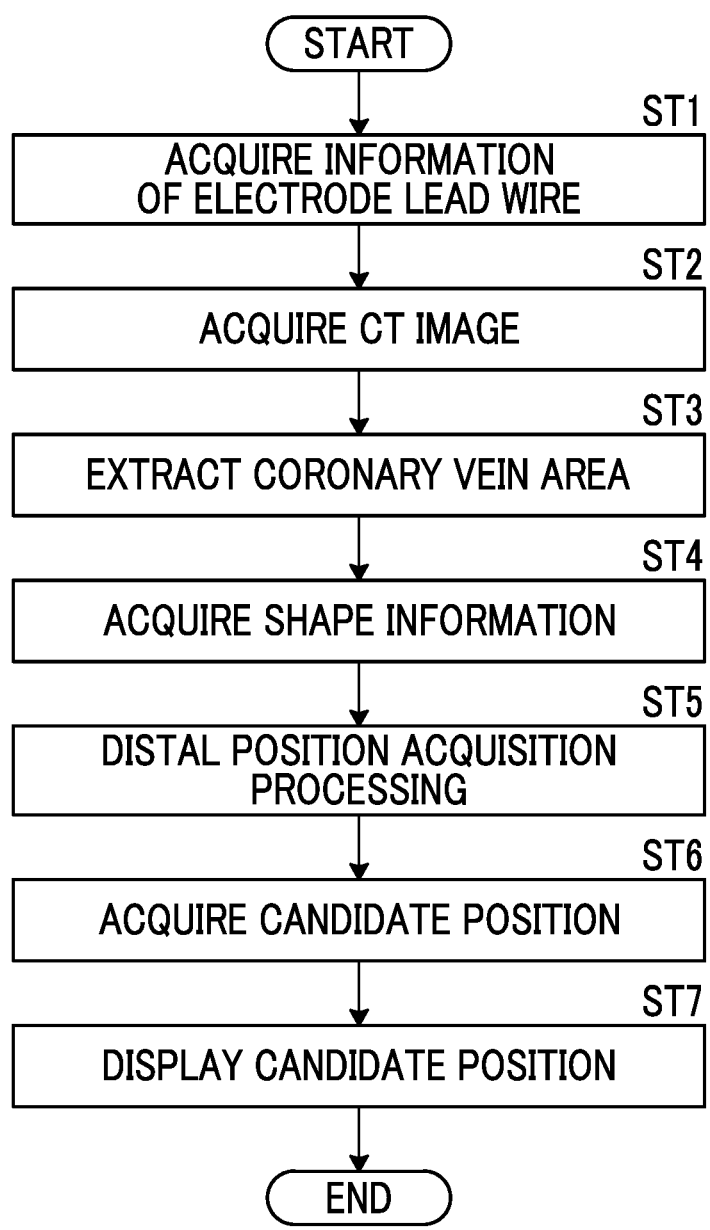
FIG. 3 is a flowchart showing processing performed in the image diagnosis support apparatus according to a first embodiment.

Next, the distal position acquisition processing performed in the first embodiment will be described. FIG. 3 is a flowchart showing the processing performed in the first embodiment. The CPU 11 acquires the diameter d and the length L of the electrode lead wire 7, and the positional information of four electrodes A1 to A4 including the interval a therebetween, which are input by the operator operating the input unit 15, as the information of the electrode lead wire 7 (step ST1). Here, the CPU 11 stores the acquired information in the storage 13. In the first embodiment, the CPU 11 acquires the information input by the operator, but the present disclosure is not limited thereto, and the CPU 11 may acquire the information of the electrode lead wire 7 from the information of a plurality of electrode lead wires 7 stored in the storage 13 in advance.

The image acquiring unit 21 acquires the CT image from the image storage server 3 as the three-dimensional image including the heart (step ST2). The shape information acquiring unit 22 extracts at least one coronary vein area from the acquired CT image by the method described above (step ST3).

The shape information acquiring unit 22 acquires size information of the diameter and the route information from the extracted coronary vein area as the shape information (step ST4).

Figure 4:
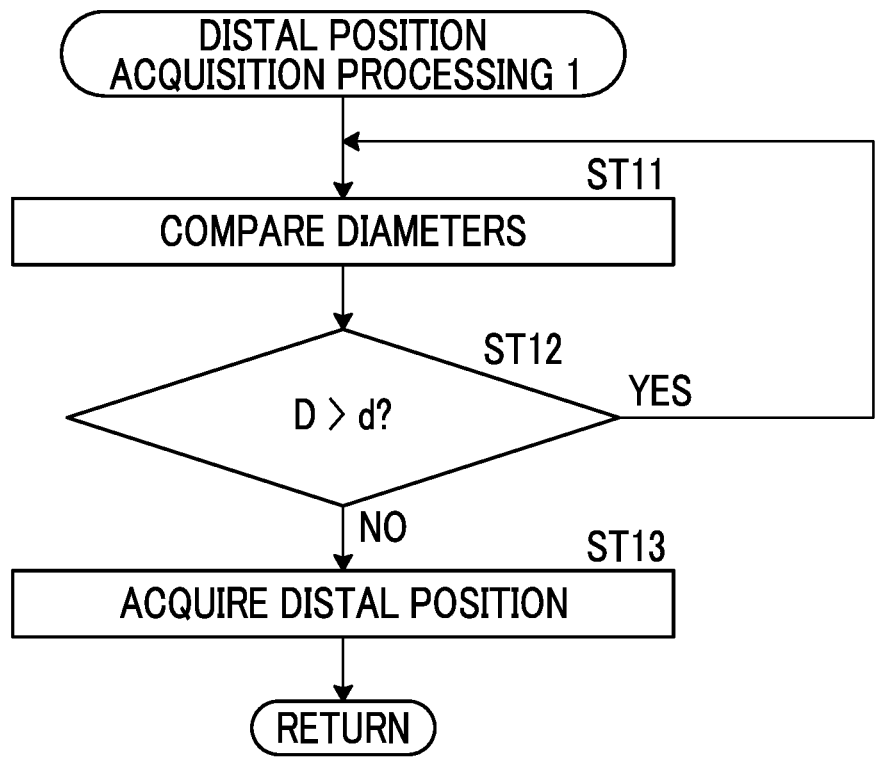
FIG. 4 is a flowchart showing distal position acquisition processing performed in the first embodiment.
Figure 5:
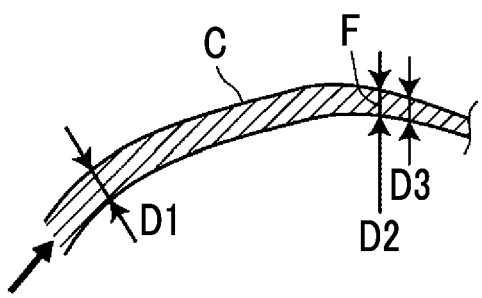
FIG. 5 is a diagram for explaining the distal position acquisition processing of FIG. 4.

The distal position acquiring unit 23 performs the distal position acquisition processing of acquiring the most distal position into which the electrode lead wire 7 can be inserted. FIG. 4 is a flowchart showing distal position acquisition processing performed in the first embodiment, and FIG. 5 is a diagram for explaining the distal position acquisition processing.

The distal position acquiring unit 23 compares the diameters, for each coronary vein area, based on the size information of the diameter of the coronary vein area and the information of the diameter d of the electrode lead wire 7 stored in the storage 13 (step ST11). As shown in FIG. 5, in a case where the direction of the arrow in FIG. 5 is the insertion direction for inserting the electrode lead wire 7 in the coronary vein area C, the distal position acquiring unit 23 compares the diameters in order from the diameter D1 on the upstream side of the coronary vein area C toward the diameter D2 on the downstream side. For example, the user designates a certain point in the coronary vein area and with the position as the origin, the diameters are compared in order toward the downstream side. In a case where the diameter D of the coronary vein area C is larger than the diameter d of the electrode lead wire 7 (step ST12; YES), the distal position acquiring unit 23 determines that the electrode lead wire 7 can be inserted in the coronary vein, the processing proceeds to step ST11, and comparison of the diameters is continuously performed.

On the other hand, in step ST12, in a case where the diameter D of the coronary vein area C is equal to or smaller than the diameter d of the electrode lead wire 7 (step ST12; NO), the distal position acquiring unit 23 determines than the electrode lead wire 7 cannot be inserted in the coronary vein, and acquires the position of the diameter D on the further upstream side, that is the position in which the determination is made that the electrode lead wire 7 can be inserted in the coronary vein, as the distal position (step ST13). The distal position may be the farthest position where the electrode lead wire can be inserted as viewed from the origin. For example, as shown in FIG. 5, in a case where the determination is made that the electrode lead wire 7 cannot be inserted in the diameter D3, the position of the diameter D2 on the further upstream side, in which the determination is made that the electrode lead wire 7 can be inserted is set to the distal position F. The distal position acquiring unit 23 acquires the distal position for all the coronary vein areas C extracted by the shape information acquiring unit 22 in the same manner as above. As described above, the distal position acquisition processing is performed by the distal position acquiring unit 23.

Figure 6:
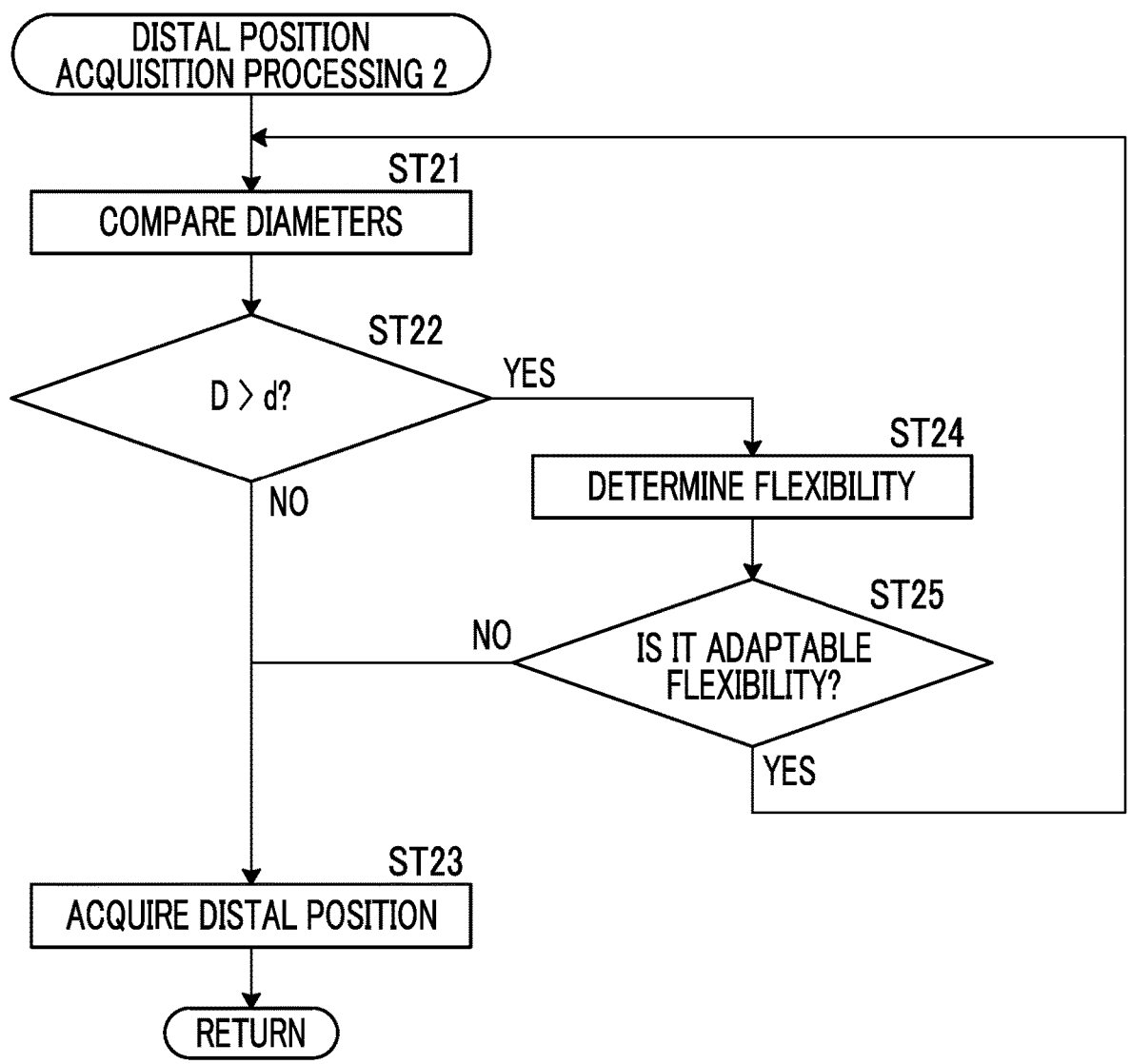
FIG. 6 is a flowchart showing distal position acquisition processing performed in a second embodiment.
Figure 7:
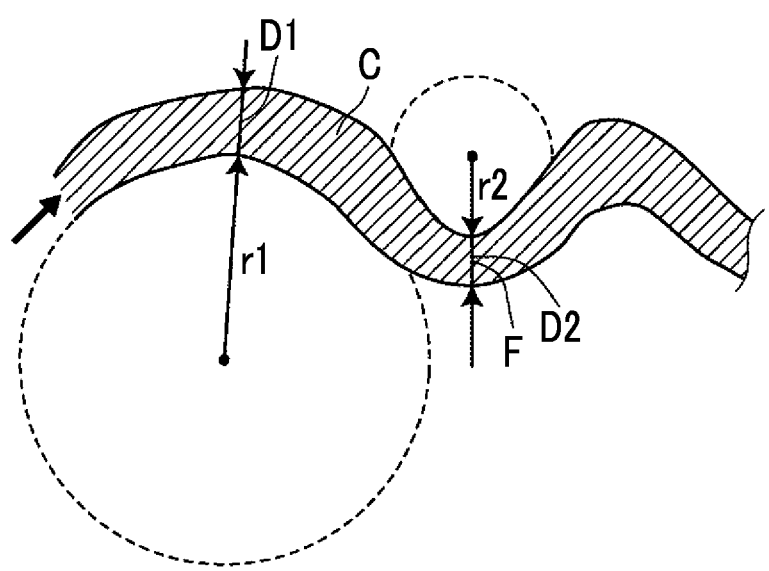
FIG. 7 is a diagram for explaining the distal position acquisition processing of FIG. 6.

In the first embodiment, the distal position acquiring unit 23 determines that the electrode lead wire 7 can be inserted in the coronary vein in a case where the diameter of the coronary vein is larger than the diameter of the electrode lead wire, but the present disclosure is not limited thereto. Hereinafter, distal position acquisition processing by the distal position acquiring unit 23 according to a second embodiment will be described. FIG. 6 is a flowchart showing distal position acquisition processing performed in the second embodiment, and FIG. 7 is a diagram for explaining the distal position acquisition processing of FIG. 6. The processing of steps ST21, ST22, and ST23 in FIG. 6 is the same as the processing of steps ST11, ST12, and ST13 in FIG. 4, and thus the description thereof will be omitted and only different processing will be described.

The distal position acquiring unit 23 according to the second embodiment determines that the electrode lead wire 7 can be inserted in the coronary vein in a case where the electrode lead wire 7 has the flexibility adaptable to the curvature of the coronary vein. In the second embodiment, the shape information acquiring unit 22 acquires size information of the diameter, the route information, and the curvature from the extracted coronary vein area as the shape information.

In step ST22, in a case where the diameter D of the coronary vein area C is larger than the diameter d of the electrode lead wire 7 (step ST22; YES), the distal position acquiring unit 23 determines the flexibility of the electrode lead wire 7 (step ST24). Specifically, the comparison of the curvatures is performed based on the information on the curvature of the coronary vein area and the information on the curvature of the electrode lead wire 7 stored in the storage 13. In the coronary vein area C, the direction of the arrow in FIG. 7 is the insertion direction for inserting the electrode lead wire 7. The distal position acquiring unit 23 compares the curvature at the position where the diameters are compared in step ST22 with the curvature of the electrode lead wire 7. In a case where the curvature l/r based on the radius r of the coronary vein area C is smaller than the curvature of the electrode lead wire 7, the distal position acquiring unit 23 determines that the flexibility of the electrode lead wire 7 is adaptable to the curvature of the coronary vein (step ST25; YES), that is, determines that the electrode lead wire 7 can be inserted in the coronary vein, the processing proceeds to step ST21, and the comparison of diameters is continuously performed.

In step ST25, in a case where the curvature l/r based on the radius r of the coronary vein area C is equal to or larger than the curvature of the electrode lead wire 7, the distal position acquiring unit 23 determines that the flexibility of the electrode lead wire 7 is not adaptable to the curvature of the coronary vein (step ST25; NO), that is, determines that the electrode lead wire 7 cannot be inserted in the coronary vein, and the processing proceeds to step ST23.

For example, as shown in FIG. 7, in step ST22, in a case where the determination is made that the electrode lead wire 7 cannot be inserted in the curve of the radius r2 at the position in which the determination is made that the diameter D2 of the coronary vein area C is larger than the diameter d of the electrode lead wire 7 (step ST22; YES), the electrode lead wire 7 cannot be bend through the curve of the radius r2, and thus the distal position acquiring unit 23 determines that the electrode lead wire 7 cannot be advanced beyond the position of the diameter D2 of the coronary vein area C, and acquires the position of the diameter D2 of the coronary vein area C as the distal position F (step ST23). The distal position acquiring unit 23 acquires the distal position F for all the coronary vein areas C extracted by the shape information acquiring unit 22 in the same manner as above. As described above, the distal position acquisition processing is performed by the distal position acquiring unit 23 according to the second embodiment.

Returning to FIG. 3, the distal position acquiring unit 23 according to the first embodiment or the second embodiment performs the distal position acquisition processing (step ST5), and then the candidate position acquiring unit 24 acquires at least one piece of information indicating the candidate positions of four electrodes A1 to A4, which are the candidates for positioning four electrodes A1 to A4 in the coronary vein, based on the distal position F acquired in step ST5 and the positional information of four electrodes A1 to A4 of the electrode lead wire 7 stored in the storage 13 (step ST6).

Figure 8A:
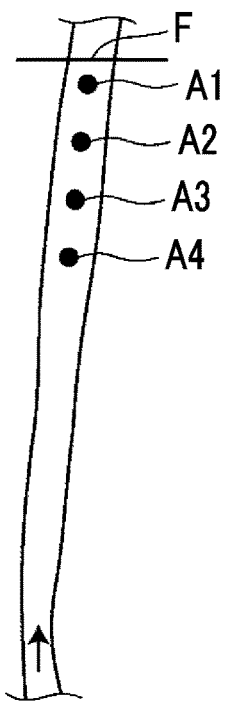
FIG. 8A is a diagram showing an example of candidate positions of electrodes.
Figure 8B:
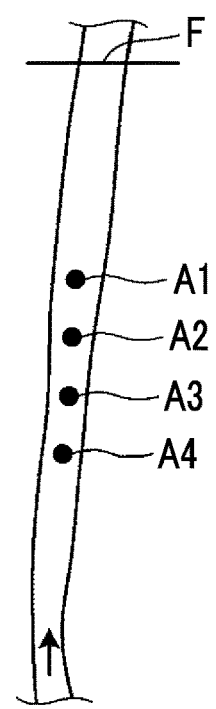
FIG. 8B is a diagram showing another example of candidate positions of electrodes.

FIGS. 8A and 8B are diagrams showing an example of the candidate positions of the electrodes. Specifically, as shown in FIG. 8A, the candidate position acquiring unit 24 acquires, as the candidate positions of the electrodes, the positions in which four electrodes A1 to A4 can be arranged while tracing back in a direction opposite from the insertion direction of the electrode lead wire 7, that is, to a proximal side from the distal position F in the coronary vein area C.

That is, as long as it is in the coronary vein area C between the insertion port of the electrode lead wire 7 and the distal position F, even in a case where the position is located on the distal position F side as shown in FIG. 8A, or the position is located away from the distal position F as shown in FIG. 8B, four electrodes A1 to A4 can be arranged at any positions. The candidate position acquiring unit 24 may position the electrode A1 on the most distal position F side at the distal position F, or at the position distant from the distal position F by a predetermined distance to the proximal side. The operator can optionally change the distance to any value using the input unit 15. The intervals a between four electrodes A1 to A4 are defined, and thus the candidate position acquiring unit 24 can acquire the arrangement positions of the electrodes A2 to A4 by acquiring the arrangement position of the electrode A1. The candidate position acquiring unit 24 may acquire one candidate position in one coronary vein area C, or also acquire the information indicating a plurality of candidate positions, such as the candidate positions shown in FIGS. 8A and 8B.

Figure 8C:
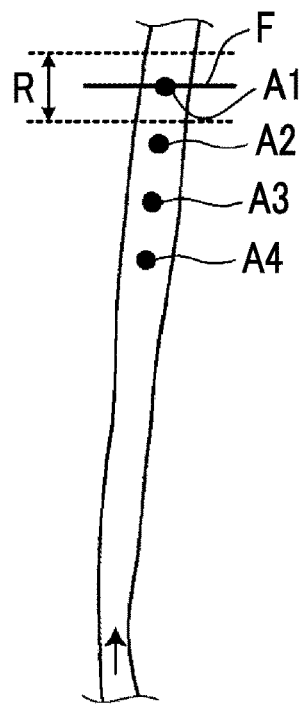
FIG. 8C is a diagram showing still another example of candidate positions of electrodes.

In the image diagnosis support apparatus according to the present disclosure, the acquisition of the information indicating the candidate position by the candidate position acquiring unit is not limited to the above. FIG. 8C is a diagram showing still another example of candidate positions of electrodes. As shown in FIG. 8C, the candidate position acquiring unit 24 may acquire, in the coronary vein area C, the information indicating the candidate position of the electrode A1 located on a most distal side among the plurality of electrodes within a predetermined range R including the distal position F. The range R may be set with the distal position F as the center, but is not limited thereto, and may be set to any position as long as the range includes the distal position F. The operator can optionally change the range R to any value using the input unit 15.

The distal position F acquired by the distal position acquiring unit 23 is the most distal side position into which the electrode lead wire 7 can be inserted in the image, but it is not always possible to insert the electrode lead wire 7 into the distal position F in a case of actually performing the surgery with respect to the subject. In some cases, the electrode lead wire 7 can actually be inserted on the distal side of the distal position F. By acquiring the candidate position of the electrode A1 within the range R including the distal position F, the position of the electrode can be brought close to the position where the electrode is placed in a case of actually performing the CRT, and thus the accuracy of the simulation can be further improved.

Figure 8D:
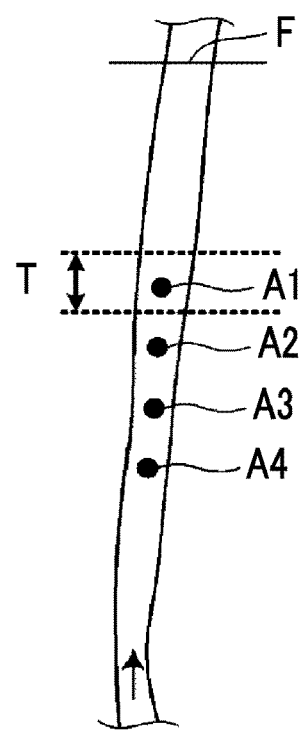
FIG. 8D is a diagram showing still another example of candidate positions of electrodes.

FIG. 8D is a diagram showing still another example of candidate positions of electrodes. As shown in FIG. 8D, the candidate position acquiring unit 24 may acquire the candidate position of the electrode A1 in a candidate range T which is predetermined, and acquire information indicating the candidate position acquired in the candidate range T which is predetermined as the information indicating the candidate position of the electrode A1.

In this case, the position of the electrode can be brought closer to the position where the electrode is placed in a case of performing CRT actually, and thus the accuracy of the simulation can be further improved. The operator can optionally change the candidate range T to any value using the input unit 15.

Figure 9:
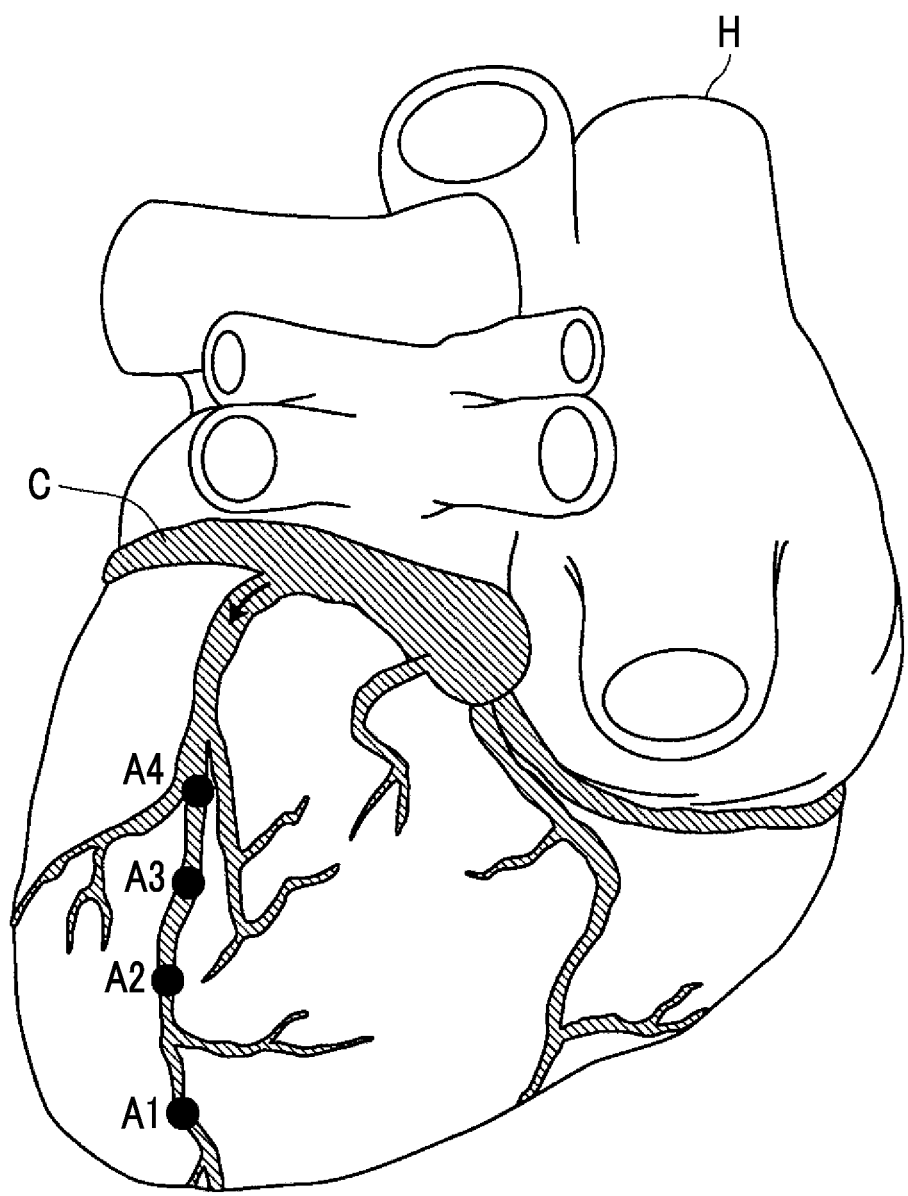
FIG. 9 is a diagram showing an example of display of candidate positions of electrodes.

Next, the display control unit 25 superimposes the candidate positions of four electrodes A1 to A4 on the CT image and displays the candidate positions on the display 14. FIG. 9 is a diagram showing an example of display of candidate positions of electrodes. As shown in FIG. 9, the display control unit 25 displays the coronary vein area C extracted by the shape information acquiring unit 22 in the heart H in the CT image by emphasizing the coronary vein area C with diagonal lines or highlights, and superimposed displays four electrodes A1 to A4 on the coronary vein area C. The display control unit 25 may sequentially display a plurality of candidate positions acquired by the candidate position acquiring unit 24 on the display 14 each time an input from the input unit 15 by the operator is detected.

In the CT image, in a case where the myocardial infarction area is detected by the analysis unit (not shown) in advance, the candidate position acquiring unit 24 may exclude the candidate position of the electrode positioned in the myocardial infarction area from the candidate for electrode arrangement. In this case, the display control unit 25 hides only the candidate position of the electrode excluded from the candidate for the electrode arrangement, for example, the electrode A1. In this way, a series of processing by the image diagnosis support apparatus 1 ends.

As described above, with the image diagnosis support apparatus 1 according to the embodiment, it is possible to decide a candidate position in which the electrode is placed in a case of actually performing the CRT, before CRT is performed. Therefore, the simulator 5 can perform the simulation at a position in which the electrode is placed in a case of actually performing the CRT, and thus the accuracy of the simulation can be improved.

Next, the simulator 5 according to the embodiment of the present disclosure will be described. In the simulator 5, the simulation program according to the present disclosure is installed in one computer. The computer may be a workstation or a personal computer directly operated by a doctor who makes a diagnosis, or a server computer connected to the workstation or the personal computer via the network. The simulation program is recorded in a recording medium such as a digital versatile disc (DVD) or a compact disc read only memory (CD-ROM) to be distributed, and is installed in the computer from the recording medium. Alternatively, the program is stored in the storage device of the server computer connected to the network or the network storage so as to be accessible from the outside, and is downloaded and installed in the computer used by a doctor upon request.

Figure 10:
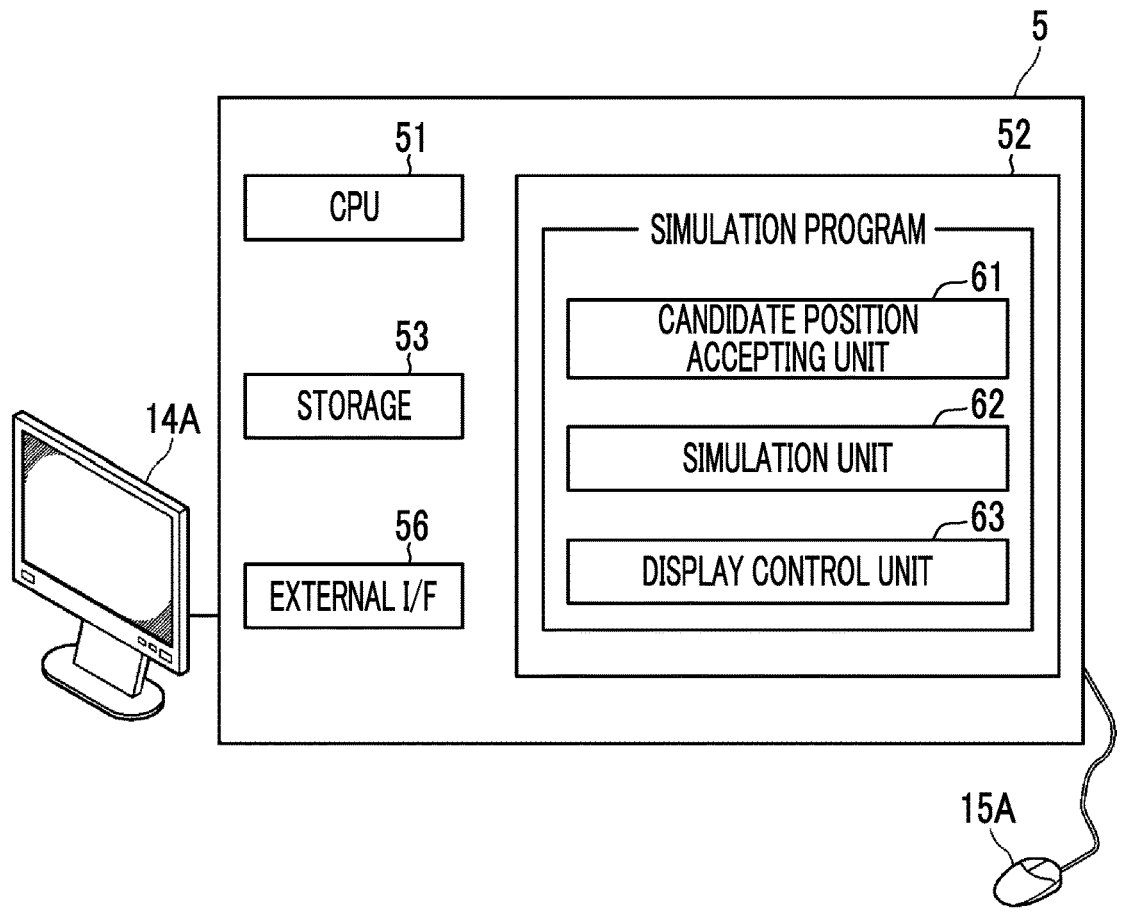
FIG. 10 is a diagram showing a schematic configuration of a simulator according to the embodiment of the present disclosure.

FIG. 10 is a diagram showing a schematic configuration of the simulator 5 according to the embodiment, which is realized by installing the simulation program in the computer. As shown in FIG. 10, the simulator 5 comprises a CPU 51, a memory 52, a storage 53, and an external I/F 56 as a standard workstation configuration. Also, the simulator 5 is connected with a display (display unit) 14A such as a liquid crystal display, and an input unit 15A such as a keyboard or a mouse.

The basic configurations of the CPU 51, the memory 52, the storage 53, and the external I/F 56 are the same as the configurations of the CPU 11, the memory 12, the storage 13, and the external I/F 16 of the image diagnosis support apparatus 1 according to the first embodiment, and the description thereof will be omitted. The external I/F 56 according to the embodiment also functions as the receiving unit according to the present disclosure which receives at least one piece of positional information of the candidate positions of the electrodes output from the image diagnosis support apparatus 1.

The simulation program is stored in the memory 52. The simulation program defines, as processing executed by the CPU 51, candidate position accepting processing of accepting at least one piece of positional information of the candidate positions of the electrodes received by the external I/F 56, simulation processing of disposing the electrodes at each candidate position of the electrode based on the accepted positional information and reproducing a cardiac motion peculiar to a patient who is a target of the CT image, and display control processing of performing control of displaying the CT image and the candidate positions of the electrodes on the display 14A.

The CPU 51 executes processing in response to the program, and the computer functions as a candidate position accepting unit 61, a simulation unit 62, and a display control unit 63.

In the embodiment, the functions of units is executed by the simulation program, but the present disclosure is not limited thereto, for example, the functions of the units may be executed by appropriate combinations of a plurality of integrated circuits (IC), a processor, an application specific integrated circuit (ASIC), a field-programmable gate array (FPGA), and the memory.

The candidate position accepting unit 61 accepts at least one piece of positional information of the candidate positions of the electrodes which are output from the image diagnosis support apparatus 1 and received by the external I/F 56.

The simulation unit 62 disposes the electrode at each candidate position of the electrode based on the one or more positional information of the candidate positions of the electrodes accepted by the candidate position accepting unit 61 and reproduces a cardiac motion peculiar to a patient who is a target of the CT image. Specifically, for example, the simulation unit 62 disposes the electrodes in the candidate positions of the electrodes displayed in FIG. 9, that is, at four electrode positions of the electrode lead wire 7, and reproduces a cardiac motion. The simulation unit 62 can use the method disclosed in Nirmal Panthee, et al., "Tailor-made heart simulation predicts the effect of cardiac resynchronization therapy in a canine model of heart failure", Medical Image Analysis 31 (2016) 46-62.

The display control unit 63 performs control of displaying the CT image and the candidate positions of the electrodes on the display 14A. The display control unit 25 performs control of displaying various information necessary for processing in the display 14A. The simulator 5 according to the embodiment is configured as above.

Next, the processing performed in the heart simulation system 10 will be described.

Figure 11:
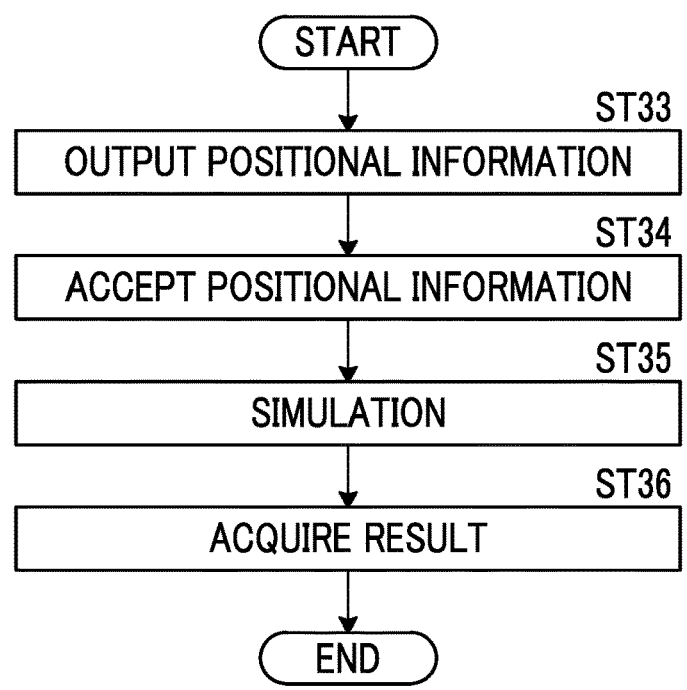
FIG. 11 is a flowchart showing processing performed in a heart simulation system according to the embodiment.

FIG. 11 is a flowchart showing processing performed in the heart simulation system. First, the image diagnosis support apparatus 1 outputs one or more positional information times of the candidate positions of the electrodes acquired by the candidate position acquiring unit 24 to the simulator 5 (step ST33).

The candidate position accepting unit 61 of the simulator 5 accepts at least one piece of positional information of the candidate positions of the electrodes which are output from the image diagnosis support apparatus 1 and received by the external I/F 56 (step ST34). The simulation unit 62 performs simulation of disposing the electrode at each candidate position of the electrode based on the one or more positional information of the candidate positions of the electrodes accepted by the candidate position accepting unit 61 and reproducing a cardiac motion peculiar to a patient who is a target of the CT image (step ST35). The simulation unit 62 acquires the simulation result for each candidate position of the electrode (step ST36). In this way, a series of processing by the heart simulation system 10 ends.

As described above, the simulator 5 can perform the simulation at the candidate position in which the electrode is placed, which are acquired by the image diagnosis support apparatus 1, that is, at the position in which the electrode is placed in a case of actually performing the CRT, and thus the accuracy of the simulation can be improved. Also, the image diagnosis support apparatus 1 acquires the information indicating the candidate positions of a plurality of electrodes, and thus the simulator 5 can perform the simulation for the candidate positions of a plurality of electrodes. Therefore, it is possible to obtain the most effective placement position of the electrode in a case of performing the CRT, and thus the cardiac function of the patient can be further improved.

In the heart simulation system 10 according to the embodiment, the image diagnosis support apparatus 1 and the simulator 5 are provided separately, but the present disclosure is not limited thereto. For example, the simulation program of the simulator 5 may be installed in the memory 12 of the image diagnosis support apparatus 1, or the image diagnosis support apparatus 1 may comprise the memory 52 of the simulator 5.

The image diagnosis support apparatus 1 according to the embodiment comprises the display 14, but the present disclosure is not limited thereto, the image diagnosis support apparatus 1 may not include the display 14. The image diagnosis support apparatus 1 can use the display 14A of the simulator 5.

In the embodiment, the shape information acquiring unit 22 extracts the coronary vein area C and the central line from the CT image, but may extract only the coronary vein area C.

In the embodiment, the CT image is used as the medical image, but the medical image is not limited thereto, and may be a MM image and a PET image.

The present disclosure is not limited to the above-described embodiments, and can be appropriately modified without departing from the spirit of the present disclosure.

EXPLANATION OF REFERENCES

1: image diagnosis support apparatus
2: three-dimensional image capturing apparatus
3: image storage server
4: network
5: simulator
7: electrode lead wire
10: heart simulation system
11, 51: CPU
12, 52: memory
13, 53: storage
14, 14A: display
15, 15A: input unit
16, 56: external I/F
21: image acquiring unit
22: shape information acquiring unit
23: distal position acquiring unit
24: candidate position acquiring unit
25, 63: display control unit
61: candidate position receiving unit
62: simulation unit
C: coronary vein area
D, D1, D2, D3: diameter of coronary vein
r, r1, r2: radius
F: distal position
A1 to A4: candidate position
H: heart
R: range
T: candidate range

What is claimed is:

1. An image diagnosis support apparatus comprising:
a processor configured to
acquire shape information including a size of a diameter and a route of a coronary vein for at least one coronary vein from a three-dimensional image including a heart;
acquire a most distal position into which an electrode lead wire is able to be inserted in an insertion direction of the electrode lead wire based on the shape information, and information indicating a size of a diameter of the electrode lead wire to compare diameters, for each coronary vein from the three-dimensional image, based on the shape information and the information indicating the size of the diameter of the electrode lead wire, wherein the electrode lead wire comprising a plurality of electrodes arranged at predetermined electrode intervals; and
acquire at least one piece of information indicating candidate positions of the plurality of electrodes which are candidates for positioning the plurality of electrodes in the at least one coronary vein based on the most distal position and positional information indicating arrangement positions of the plurality of electrodes.

2. The image diagnosis support apparatus according to claim 1,
wherein the processor is configured to acquire, a piece of information indicating the candidate positions of the plurality of electrodes at positions traced back to a proximal side from the most distal position on the route of the coronary vein.

3. The image diagnosis support apparatus according to claim 2,
wherein the processor is configured to acquire the candidate positions of the plurality of electrodes in a predetermined candidate range, as the information indicating the candidate positions of the plurality of electrodes.

4. The image diagnosis support apparatus according to claim 2,
wherein the processor is configured to acquire the information indicating the candidate positions of the plurality of electrodes at positions distant from the most distal position by a predetermined distance to the proximal side.

5. The image diagnosis support apparatus according to claim 2,
wherein the processor enables insertion of the electrode lead wire in the coronary vein in response to the diameter of the coronary vein is larger than the diameter of the electrode lead wire.

6. The image diagnosis support apparatus according to claim 1,
wherein the processor is configured to acquire, a piece of the information indicating the candidate positions of the plurality of electrodes located on a most distal side among the plurality of electrodes within a predetermined range including the most distal position.

7. The image diagnosis support apparatus according to claim 6,
wherein the processor is configured to acquire the candidate positions of the plurality of electrodes in a predetermined candidate range, as the information indicating the candidate positions of the plurality of electrodes.

8. The image diagnosis support apparatus according to claim 6,
wherein the processor is configured to acquires the information indicating the candidate positions of the plurality of electrodes at positions distant from the most distal position by a predetermined distance to a proximal side.

9. The image diagnosis support apparatus according to claim 6,
wherein the processor enables insertion of the electrode lead wire in the coronary vein in response to the diameter of the coronary vein is larger than the diameter of the electrode lead wire.

10. The image diagnosis support apparatus according to claim 1,
wherein the processor is configured to acquire the candidate positions of the plurality of electrodes in a predetermined candidate range, as the information indicating the candidate positions of the plurality of electrodes.

11. The image diagnosis support apparatus according to claim 10,
wherein the processor is configured to acquires the information indicating the candidate positions of the plurality of electrodes at positions distant from the most distal position by a predetermined distance to a proximal side.

12. The image diagnosis support apparatus according to claim 1,
wherein the processor determines to enable insertion of the electrode lead wire in the at least one coronary vein in response to the diameter of the coronary vein is larger than the diameter of the electrode lead wire.

13. The image diagnosis support apparatus according to claim 1,
wherein the electrode lead wire has flexibility, and
the processor determines to enable insertion of the electrode lead wire in the at least one coronary vein in response to the electrode lead wire has the flexibility adaptable to a curvature of the coronary vein.

14. The image diagnosis support apparatus according to claim 1, wherein the processor is configured to exclude a candidate position from the candidate positions of the plurality of electrodes in response to the candidate position of the electrode is located within a myocardial infarction area in the three-dimensional image.

15. The image diagnosis support apparatus according to claim 1, the processor further configured to perform control of displaying the three-dimensional image and the candidate position of the electrode on a display unit.

16. The image diagnosis support apparatus according to claim 15, wherein the processor is configured to perform control of displaying the candidate positions of the plurality of electrodes while superimposing the candidate positions of the plurality of electrodes on the three-dimensional image.

17. The image diagnosis support apparatus according to claim 1, the processor further configured to output the at least one piece of positional information indicating the candidate positions of the plurality of electrodes.

18. A heart simulation system comprising:
the image diagnosis support apparatus according to claim 17; and
a simulator that includes an interface receiving at least one piece of positional information of the candidate positions of the plurality of electrodes output from the image diagnosis support apparatus, and disposes an electrode at each candidate position of the plurality of electrodes based on the at least one piece of positional information of the candidate positions of the plurality of electrodes received by the interface, and reproduces a cardiac motion peculiar to a patient who is a target of the three-dimensional image.

19. An image diagnosis support method comprising:
acquiring shape information including a size of a diameter and a route of a coronary vein for at least one coronary vein from a three-dimensional image including a heart;
acquiring a most distal position into which an electrode lead wire is able to be inserted in an insertion direction of the electrode lead wire based on the shape information, and information indicating a size of a diameter of the electrode lead wire to compare diameters, for each coronary vein from the three-dimensional image, based on the shape information and the information indicating the size of the diameter of the electrode lead wire, wherein the electrode lead wire comprising a plurality of electrodes arranged at predetermined electrode intervals; and
acquiring at least one piece of information indicating candidate positions of the plurality of electrodes which are candidates for positioning the plurality of electrodes in the at least one coronary vein based on the most distal position and positional information indicating arrangement positions of the plurality of electrodes.

20. A non-transitory computer readable recording medium storing an image diagnosis support program causing a computer to execute:
a procedure of acquiring shape information including a size of a diameter and a route of a coronary vein for at least one coronary vein from a three-dimensional image including a heart;
a procedure of acquiring a most distal position into which an electrode lead wire is able to be inserted in an insertion direction of the electrode lead wire based on the shape information, and information indicating a size of a diameter of the electrode lead wire to compare diameters, for each coronary vein from the three-dimensional image, based on the shape information and the information indicating the size of the diameter of the electrode lead wire, wherein the electrode lead wire comprising a plurality of electrodes arranged at predetermined electrode intervals; and
a procedure of acquiring at least one piece of information indicating candidate positions of the plurality of electrodes which are candidates for positioning the plurality of electrodes in the at least one coronary vein based on the most distal position and positional information indicating arrangement positions of the plurality of electrodes.

* * * * *